United States Patent
Wongsarnpigoon et al.

(10) Patent No.: US 10,625,075 B2
(45) Date of Patent: Apr. 21, 2020

(54) SYSTEMS AND METHODS RELATED TO THE TREATMENT OF BACK PAIN

(71) Applicant: SPR Therapeutics, Inc., Cleveland, OH (US)

(72) Inventors: Amorn Wongsarnpigoon, Chapel Hill, NC (US); Maria Bennett, Beachwood, OH (US); Joseph W. Boggs, Chapel Hill, OH (US); John Chae, Strongsville, OH (US); Michael F. Saulino, Havertown, PA (US)

(73) Assignee: SPR THERAPEUTICS, INC., Cleveland, OH (US)

(*) Notice: Subject to any disclaimer, the term of this patent is extended or adjusted under 35 U.S.C. 154(b) by 0 days.

(21) Appl. No.: 13/843,002

(22) Filed: Mar. 15, 2013

(65) Prior Publication Data
US 2013/0296966 A1    Nov. 7, 2013

Related U.S. Application Data

(60) Provisional application No. 61/611,560, filed on Mar. 15, 2012.

(51) Int. Cl.
*A61N 1/36* (2006.01)
*A61N 1/05* (2006.01)

(52) U.S. Cl.
CPC ....... *A61N 1/36021* (2013.01); *A61N 1/0558* (2013.01); *A61N 1/36071* (2013.01)

(58) Field of Classification Search
USPC .......................................... 607/46, 117, 118
See application file for complete search history.

(56) References Cited

U.S. PATENT DOCUMENTS

| | | | |
|---|---|---|---|
| 6,845,271 | B2 | 1/2005 | Fang et al. |
| 7,337,005 | B2 | 2/2008 | Kim et al. |
| 7,761,166 | B2 | 7/2010 | Giftakis et al. |
| 7,792,591 | B2 | 9/2010 | Rooney et al. |
| 8,249,713 | B2 | 8/2012 | Fang et al. |
| 2005/0240243 | A1 | 10/2005 | Barolat et al. |
| 2007/0027501 | A1 | 2/2007 | Jenson et al. |
| 2008/0228241 | A1 | 9/2008 | Sachs |
| 2010/0036454 | A1 | 2/2010 | Bennett et al. |
| 2010/0152808 | A1 | 6/2010 | Boggs, II |
| 2010/0152809 | A1 | 6/2010 | Boggs, II |
| 2010/0241195 | A1* | 9/2010 | Meadows ............ A61N 1/0556 607/62 |

(Continued)

OTHER PUBLICATIONS

International Search Report and the Written Opinion of the International Searching Authority, SPR Therapeutics, LLC, dated Jun. 4, 2013.

(Continued)

*Primary Examiner* — Joseph M Dietrich
(74) *Attorney, Agent, or Firm* — McDonald Hopkins LLC

(57) ABSTRACT

The present invention reduces pain and improves function long-term in persons with back pain using electrical stimulation in the back. This approach involves an electrical stimulation device including at least one electrode adapted for insertion within an animal body with back pain and at least one pulse generator operatively coupled with the at least one electrode, wherein the pulse generator delivers electrical stimulation activating at least one muscle in a back of the animal body for pain relief.

19 Claims, 17 Drawing Sheets

(56) References Cited

U.S. PATENT DOCUMENTS

| | | | |
|---|---|---|---|
| 2011/0021943 A1* | 1/2011 | Lacour | A61N 1/0551 600/546 |
| 2011/0224665 A1 | 9/2011 | Crosby et al. | |
| 2012/0016439 A1 | 1/2012 | Alataris et al. | |
| 2012/0290055 A1 | 11/2012 | Boggs, II | |
| 2012/0310301 A1 | 12/2012 | Bennett et al. | |
| 2012/0310302 A1 | 12/2012 | Bennett et al. | |
| 2012/0310314 A1 | 12/2012 | Bennett et al. | |
| 2013/0096641 A1 | 4/2013 | Strother | |
| 2013/0197615 A1 | 8/2013 | Rundle | |

OTHER PUBLICATIONS

U.S. Appl. No. 13/605,653, filed Sep. 6, 2012, Inventors: Joseph W. Boggs, II, et al.
U.S. Appl. No. 13/843,002, filed Aug. 7, 2013, Inventors: Amorn Wongsarnpigoon, et al.
European Patent Office, Extended European Search Report for Application 13760774.3, PCT/US2013/032627, dated Jan. 5, 2016, 11 pgs., European Patent Office, Germany.

\* cited by examiner

X= Electrode Location

X= Electrode Location

SYSTEMS AND METHODS RELATED TO THE TREATMENT OF BACK PAIN

CROSS-REFERENCE TO RELATED APPLICATION

This application claims the benefit from U.S. Provisional Patent Application Ser. No. 61/611,560 entitled "Systems and Methods Related to the Treatment of Back Pain" filed on Mar. 15, 2012, which is hereby incorporated in its entirety by reference.

FIELD OF INVENTION

The present invention generally relates to a system and a method to deliver percutaneous stimulation to relieve pain and improve function in patients with back pain.

BACKGROUND OF THE INVENTION

Back pain (e.g., low back pain (LBP) lasting approximately 12 weeks) affects approximately tens of millions of people in the U.S. and is the second leading cause of disability (6.8 million people). Back pain is associated with reduced activities of daily living (e.g., walking, housework, personal care) and health-related quality of life. In addition, back pain is expensive to treat and often leads to missed work days (149 million days/year) and reduced productivity, resulting in total costs of $100-200 billion/year in the U.S.

Present methods to relieve back pain are ineffective, expensive, inconvenient, and/or invasive. For example, oral medications (e.g., acetaminophen, NSAIDs, muscle relaxants, tricyclic antidepressants, antiepileptics, and corticosteroids) provide only limited and/or short-lived pain relief, and typically produce side effects (e.g., sedation, dizziness, and gastrointestinal problems). Although opioids can provide substantial short-term pain relief, they are not recommended as a treatment to control chronic back pain, since long-term use can result in dependence and severe side effects.

Exercise (including yoga, stretching, strength training) has a low level of risk and can relieve pain and improve function long-term, but patients often fail to comply with treatment regimens due to discomfort, lack of motivation, and inconvenience.

Physical manipulation (i.e., massage, spinal manipulation) has a low level of risk and can provide short-term pain relief. However, evidence for the long-term benefit of physical manipulation has been mixed. Further, frequent treatment sessions are required to maintain pain relief, which is inconvenient for patients.

Acupuncture is minimally-invasive, and studies have suggested that acupuncture can provide pain relief. However, study design in acupuncture studies has been questionable (e.g., adequacy of sham/placebo/control), and the effectiveness of acupuncture remains controversial.

Injections of steroids or anesthetic provide short-term pain relief but seldom produce long-term benefit. As well, injections of such medicines produce side effects, including increased pain, lightheadedness, headache, infection, and nausea and vomiting.

Intrathecal drug therapy can be effective for reducing pain but requires an invasive procedure and is limited by a host of frequent side effects (e.g., nausea, infection, intrathecal granuloma). Also, technical complications (i.e., problems with catheter or pump) are common and may require reoperation or removal of the device.

Surgical procedures for back pain (e.g., spinal fusion, disc replacement) are highly invasive, irreversible, carry risks of complications, and reduce pain in less than half of patients. Also, surgeries for chronic back pain frequently require reoperation.

Existing methods of electrical stimulation reduce pain by generating paresthesias (i.e., tingling sensation) overlapping the regions of pain. Pain relief using these existing methods persists only for a short time following treatment (e.g., hours to days), and this suggests that chronic pain has not been reversed. As a result, only a small percentage of patients using existing methods of electrical stimulation experienced clinically significant reductions in chronic axial low back pain post-treatment.

TENS is a non-invasive method to deliver electrical stimulation through surface electrodes to generate paresthesia coverage of the regions of pain. TENS requires frequent treatment sessions to maintain pain relief, but consistent efficacy in chronic low back pain has not been demonstrated. Although TENS can be self-administered at home, TENS systems are cumbersome and not practical for daily use. Also, TENS can activate cutaneous fibers and cause irritation and discomfort, limiting the maximum tolerable stimulation intensity and treatment duration that can be delivered and reducing the potential efficacy of the treatment.

Spinal cord stimulation is a method to deliver electrical stimulation through implanted leads connected to an implanted pulse generator to generate paresthesia coverage of the regions of pain. Spinal cord stimulation requires complex and invasive surgery to implant the leads and pulse generator. Spinal cord stimulation has a moderate rate of complications, including additional pain and hardware complications, and as a result, revision surgery, reprogramming, or removal of the stimulator is often required.

In summary, present treatments for back pain seldom provide adequate long-term relief of pain or improvements in function; carry risks of side effects and complications; and/or are invasive.

There remains room in the art of pain management for unproved systems and methods to be used to assist in the treatment of back pain.

SUMMARY OF THE INVENTION

Embodiments according to the present invention provide improved systems and methods to be used to assist in the treatment of back pain.

The invention provides an electrical stimulation device having at least one electrode adapted for insertion within an animal body with back pain and at least one pulse generator operatively coupled with the at least one electrode, wherein the pulse generator delivers electrical stimulation activating at least one muscle in a back of the animal body for pain relief.

The invention also provides an electrical stimulation device having at least one electrode adapted for insertion below skin of an animal body with back pain and a pulse generator operatively coupled with the at least one electrode, wherein the pulse generator delivers electrical stimulation for a prescribed period of time to activate at least one muscle in a back of the animal body to relive pain.

The invention further provides a method to alleviate back pain including placing at least one electrode within a tissue of an animal body, and applying stimulation through the at least one electrode to activate at least one muscle in a back of the animal body with back pain.

Other features and advantages of the inventions are set forth in the following specification and attached drawings.

BRIEF DESCRIPTION OF THE DRAWINGS

Operation of the invention may be better understood by reference to the detailed description taken in connection with the following illustrations, wherein.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with each other in any combination.

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

The stimulation system discussed below involves inserting an electrode into an animal body and using electrical stimulation to activate a muscle to provide pain relief. Any method of electrical stimulation will work to activate the at least one muscle in the body.

Figure 1:
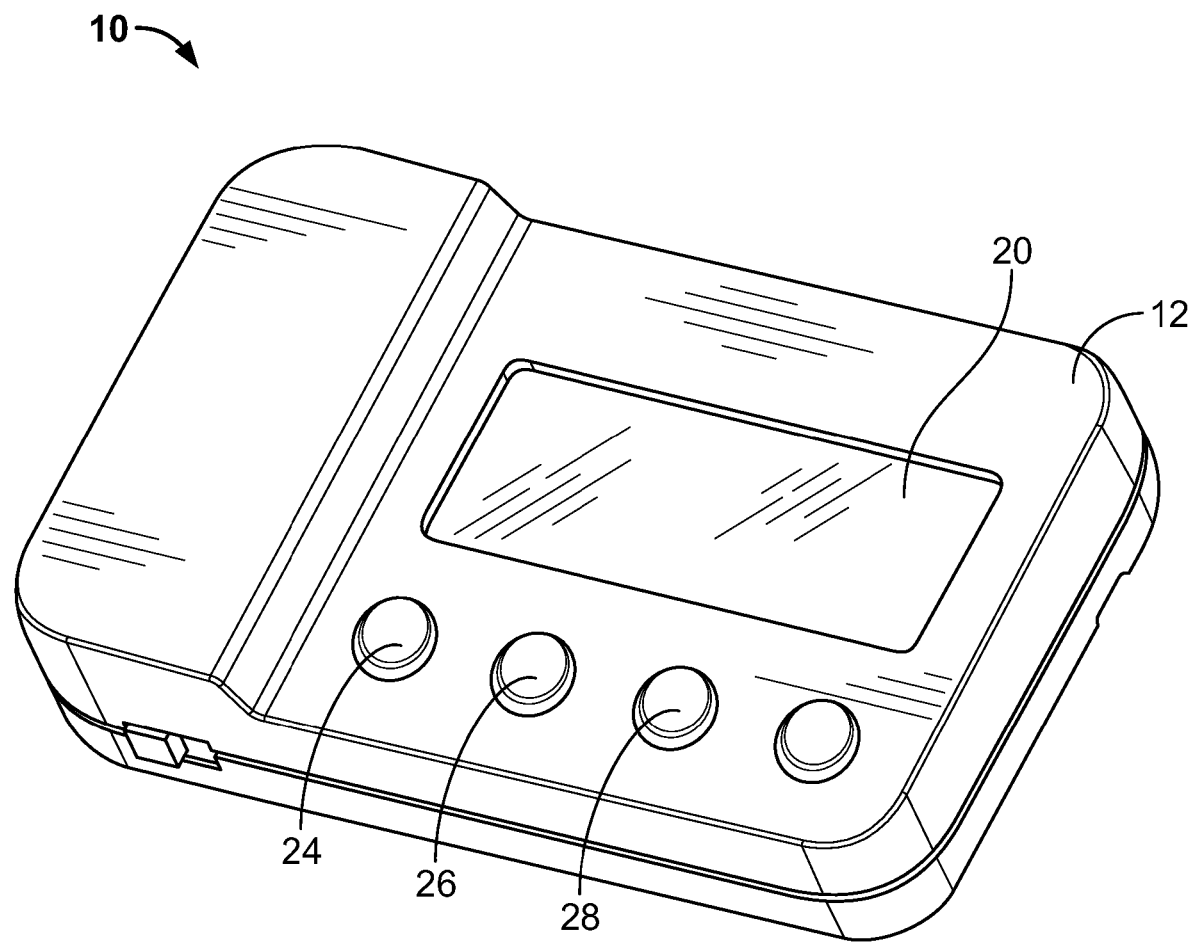
FIG. 1 is a frontal view of a stimulation pulse train generator.

With reference to FIG. 1, a percutaneous stimulation system is shown that can be used with the method of treating the back in accordance with the present teachings. The stimulator may include an electrical stimulation pulse generator 10. The pulse generator 10 may include a lightweight, durable housing 12 that may be fabricated from a suitable plastic or the like. In some embodiments, the case 12 may include a clip that allows the pulse generator 10 to be releasably connected to a patient's belt, other clothing, or any other convenient location. The case 12 may also include a releasable battery access cover. Other means of securing the stimulator may be used that allow the stimulator to be secured to the patient's skin without and/or under clothing (e.g., adhesive, magnet, etc.).

For output of data to a patient or clinician operating the stimulation system, a visual display 20 may be provided. The display 20 may be by a liquid crystal display, but any other suitable display may alternatively be used. An audio output device, such as a beeper may also be provided. Alternatively, data may be conveyed to the user in other ways (e.g., tactile, flashing LEDs).

For user control, adjustment, and selection of operational parameters, the stimulation pulse generator 10 may include a mechanism or device for input of data. The pulse generator 10 may include an increment switch 24, a decrement switch 26, and a select or "enter" switch 28. The increment and decrement switches 24, 26 may be used to cycle through operational modes or patterns and stimulation parameters displayed on the display 20, while the select switch 28 may be used to select a particular displayed operational pattern or stimulation parameter. The select switch 28 may also act as a power on/off toggle switch.

For output of electrical stimulation pulse train signals, the pulse train generator 10 may include an external connection socket (not shown) that may mate with a connector of an electrode cable assembly (not shown) to interconnect the pulse generator 10 with a plurality of electrodes, such as through use of percutaneous electrode leads. More particularly the cable assembly connected to the socket 30 may include a second connector such as on a distal end that may mate with a connector attached to the proximal end of each of the percutaneous stimulation electrode leads and a reference electrode lead. Alternatively, the pulse generator may transmit signals without a physical connection to the electrode (e.g., radio-frequency coupling, passive polarization of electrode) or may be housed within a single unit along with the electrode.

Figure 2:
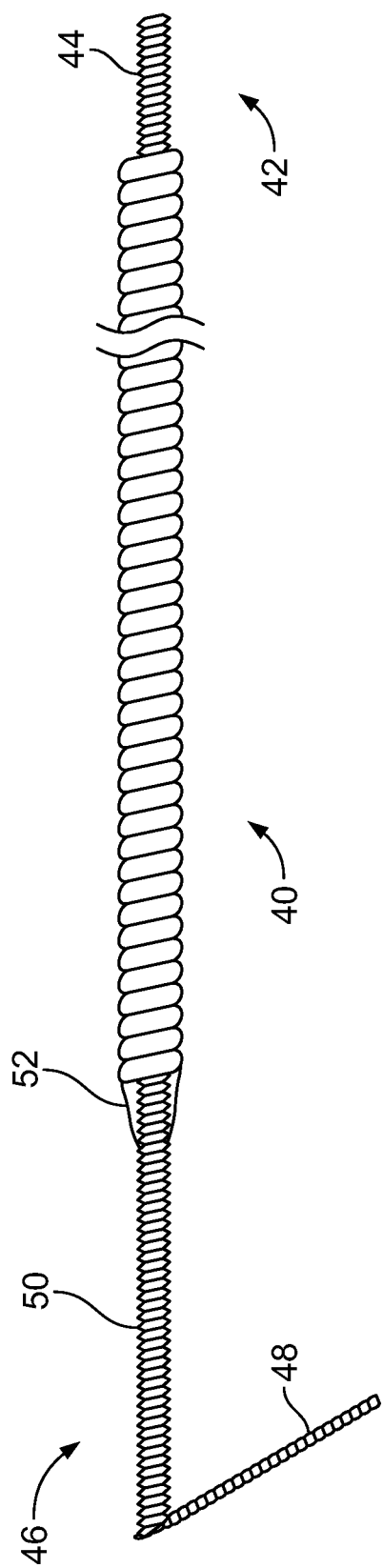
FIG. 2 is a top view of an electrode and percutaneous electrode lead.

Exemplary embodiments of an electrode and percutaneous lead are shown in FIG. 2. The electrode lead 40 may be fabricated from a 7-strand stainless steel wire insulated with a biocompatible polymer. Each individual wire strand may have a diameter of approximately 34 μm and the insulated multi-strand lead wire may have a diameter of approximately 250 μm. It should be understood, however, that these dimensions are merely exemplary and the present teachings are not limited to such. Any appropriate sized, shaped and configured electrode and percutaneous lead may be used. The insulated wire may be formed into a spiral or helix as has been found to accommodate high dynamic stress upon muscle flexion and extension, while simultaneously retaining low susceptibility to fatigue. The outer diameter of the helically formed electrode lead 40 may be approximately 580 μm and it may be encased or filled with silicone or the like. Alternatively, the lead may have additional or fewer strands, may be made out of a different material (e.g., another metal, conducting polymer), may be insulated with another material, or may not be insulated. Further, the lead may be the same type of use for spinal cord stimulation (e.g., cylindrical or paddle-type leads).

As mentioned above, a proximal end 44 of each of the plurality of electrode lead wires 40 may be located exterior to the patient's body when in use. The proximal end 44 may include a deinsulated length for connection to an electrical connector in combination with the remainder of the electrode leads. The deinsulated portion may be located on any portion of the proximal portion of the lead located outside of the body. In some embodiments, the distal end 46 of each lead 40, which may be inserted directly into tissue, may also include a deinsulated length. The deinsulated length may act as the stimulation electrode 50. At least a portion of the deinsulated length may be bent or otherwise deformed into a barb 48. This may anchor the electrode in the selected tissue. A taper 52, made from silicone adhesive or the like, may be formed between the deinsulated distal end 50 and the insulated portion of the lead 40 to reduce stress concentration. The electrode may be placed anywhere along the length of the lead; the present teachings are not limited to the aforementioned locations. The electrode may be a conductive contact connected (e.g., welded, via adhesive) to the lead. Alternatively, the lead may be threaded (i.e., like a screw), and may be screwed into the tissue, which will mechanically secure the lead in the tissue.

Unlike surface electrodes that are applied to the surface of the patient's skin using an adhesive, each of the plurality of percutaneous electrodes 50 may be surgically implanted or otherwise inserted into select patient's tissue. The associated electrode lead 40 may exit the patient percutaneously, i.e., through the skin, for connection to the stimulation pulse generator 10. Each of the electrodes 50 may be implanted or otherwise inserted into the select tissues by use of a needle. The needle may be straight or may be hooked. Alternatively, the lead may be inserted using other hollow tubes (e.g., cannula, catheter) or may be "shot" out of a device at sufficiently high speeds such that a rigid structure (e.g., needle) is not needed to penetrate the skin. Alternatively, the lead may be introduced through a vessel (e.g., vein, artery). Alternatively, the lead itself may be rigid, enabling the lead to be insertable into the tissue without another object (e.g., a needle). Alternatively, or in addition, tissues may be surgically exposed for implantation or minimally invasive techniques such as arthroscopy may be used. Alternatively, multiple electrodes may be on an array (e.g., paddle electrode, cylindrical electrode, array of needles, etc.). Once all of the electrodes are implanted as desired, their proximal ends may be crimped into a common connector that may mate with the cable assembly. The cable assembly may be, in turn, connected to the pulse generator 10 through the connection socket 30. Alternatively, the electrodes may be connected directly to the stimulator. Alternatively, each electrode may be connected to an individual connector. Alternative means of securing the leads to the connector may also be used (e.g., magnetic, adhesive). Alternatively, the proximal ends of the leads may terminate on a plug (e.g., banana plug, BNC plug) that can be connected to the stimulator either directly or via a connector. Such therapies or uses may require multiple systems, which utilize multiple pulse train generators with multiple common connectors.

The present percutaneous stimulation system may allow for precise selection of muscle stimulation and use of two or more stimulation electrodes and channels. Alternatively, a system may use one stimulation electrode. The system in accordance with the present invention may use two or more electrodes 50, each connected to an independent electrode stimulation channel E, and a single reference electrode 52 that may be a percutaneous, surface electrode, the case of the stimulator (if implanted), or an implanted electrode. Alternatively, there may be more than one reference electrode, and each stimulation channel may have its own reference electrode. The electrode stimulation channels may not be independent, i.e., the same stimulation may be delivered to multiple channels at once.

The stimulation pulse generator 10 may include a microprocessor-based stimulation pulse generator circuit with a micro controller such as a Motorola 68HC12. Operational instructions or other information may be stored in non-volatile storage. Set stimulation therapy or patterns may be included in this storage. These therapies may be based upon generalized information such as may be gathered from radiographic evaluation in multiple dimensions along with selected stimulation. Ultimately patient specific information may be incorporated into the stimulation parameters in order to optimize the therapy for a particular individual application. Preferably, the nonvolatile memory may also provide storage for all patient-specific stimulation protocols. A real time clock may be provided as part of the circuit.

The electrical stimulator current may pass between the selected electrodes and the reference electrode(s). A pulse duration timer may provide timing input PDC as determined by the CPU to the pulse amplitude/duration controller to control the duration of each stimulation pulse. Likewise, the CPU may provide a pulse amplitude control signal to the circuit by way of the serial peripheral interface to control the amplitude of each stimulation pulse.

Each output channel E1-E2 may include independent electrical charge storage such as a capacitor SC that is charged to the high voltage VH through a respective current limiting diode CD. To generate a stimulation pulse, the microcontroller output circuit 102 may provide channel select input data to switch component, as to the particular channel E1-E2 on which the pulse may be passed. Switch SW may close the selected switch SW1-SW2 accordingly. The microcontroller may also provide a pulse amplitude control signal PAC into a voltage-controlled current source VCCS. As such, the pulse amplitude control signal PAC may control the magnitude of the current I, and the circuit VCCS may ensure that the current I is constant at that select level as dictated by the pulse amplitude control input PAC. For stimulation of human muscle, the current I may be within an approximate range of 1 mA-20 mA. However, the present teachings are not limited to such range. Any appropriate range may be used with the present teachings.

Upon completion of the cathodic phase Qc as controlled by the pulse duration control signal PDC, the discharged capacitor SC may recharge upon opening of the formerly closed one of the switches SW1-SW2. The flow of recharging current to the capacitor SC may result in a reverse current flow between the relevant electrode 50 and the reference electrode 52, thus defining an anodic pulse phase Qa. The current amplitude in the anodic pulse phase Qa is limited, preferably to 0.5 mA, by the current limiting diodes CD. Of course, the duration of the anodic phase may be determined by the charging time of the capacitor SC, and current flow may be blocked upon the capacitor becoming fully charged. It should be recognized that the interval between successive pulses or pulse frequency PF may be controlled by the CPU 62 directly through output of the channel select, pulse amplitude, and pulse duration control signals as described at a desired frequency PF.

Some embodiments may implement from 1 to 8 or more independent preprogrammed patterns. For each pattern, a stimulation session S may be pre-programmed into the stimulator circuit by a clinician through use of the input device. Each session S may have a maximum session duration of approximately 24 hours, and a session starting delay D. However, it should be understood that these parameters are merely exemplary and not exhaustive or exclusive.

Figure 3:
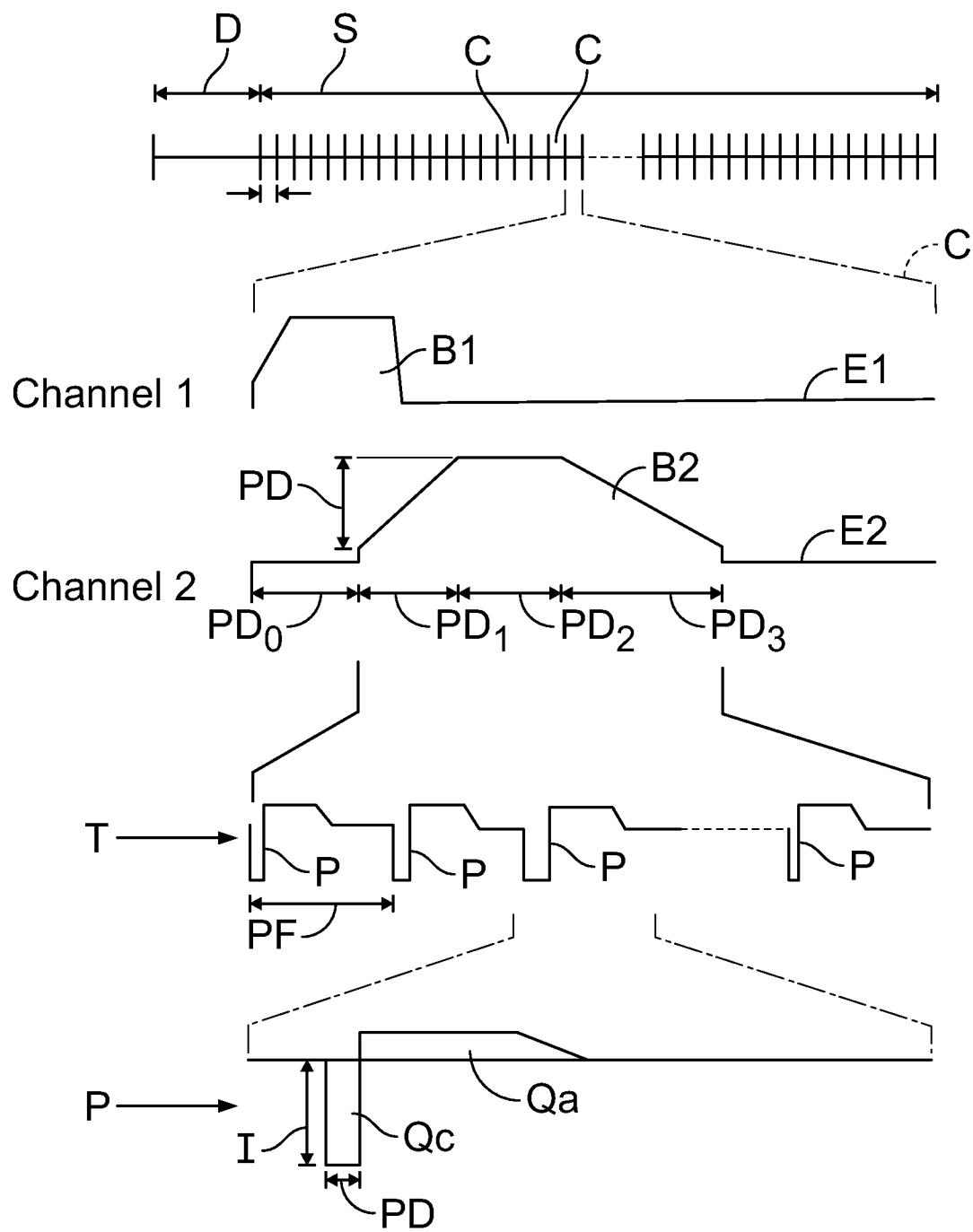
FIG. 3 graphically illustrates the stimulation paradigm of a percutaneous stimulation system.

With continuing reference to FIG. 3, a stimulus pulse train T may include a plurality of successive stimulus pulses P. A stimulus pulse P may be current-regulated. It may also be biphasic, i.e., comprises a cathodic charge phase Qc and an anodic charge-phase Qa. Alternatively, the stimulus pulse may be monophasic, i.e., comprises only a cathodic charge phase or anodic charge phase, or contain more than 2 phases. The magnitude of the cathodic charge phase(s) Qc, may be equal to the magnitude of the anodic charge phase(s) Qa. The current-regulated, biphasic pulses P may provide for consistent muscle recruitment along with minimal tissue damage and electrode corrosion. Alternatively or in addition to, a stimulus pulse may be regulated by other parameters (e.g., voltage-regulated, charge-regulated).

Each pulse P may be defined by an adjustable current I (or voltage for voltage-regulated, or charge for charge-regulated, etc.) and an adjustable pulse duration PD. The pulse frequency PF may also be adjustable. Further, the current I, pulse duration PD, and pulse frequency PF may be independently adjustable for each stimulation channel E. The amplitude of the anodic charge phase Qa may be fixed, but may be adjusted if desired.

Pulse "ramping" may be used at the beginning and/or end of each stimulation pulse train T to generate smooth muscle contraction, but other methods may be used as well. Ramping is defined herein as the gradual change in cathodic pulse charge magnitude by varying at least one of the current I and pulse duration PD. In FIG. 3, an embodiment of a ramping configuration is illustrated in greater detail. As mentioned, each of the plurality of stimulation leads/electrodes 40, 50 may be connected to the pulse generator circuit 60 via a stimulation pulse channel E. As illustrated in FIG. 3, two stimulation pulse channels E1 and E2 may be provided to independently drive up to two electrodes 50. Stimulation pulse trains transmitted on each channel E1 and E2 may be transmitted within or in accordance with a stimulation pulse train envelope B1-B2, respectively. The characteristics of each envelope B1-B2 may be independently adjustable by a clinician for each channel E1-E2. Referring particularly to the envelope B2 for the channel E2, each envelope B1-B2 may be defined by a delay or "off" phase PD0 where no pulses are delivered to the electrode connected to the subject channel, i.e., the pulses have a pulse duration PD of 0. Thereafter, according to the parameters programmed into the circuit 60, the pulse duration PD of each pulse P is increased or "ramped-up" over time during a "ramp-up" phase PD1 from a minimum value (e.g., 5 μsec) to a programmed maximum value. In a pulse duration "hold" phase PD2, the pulse duration PD remains constant at the maximum programmed value. Finally, during a pulse duration "ramp-down" phase PD3, the pulse duration PD of each pulse P may be decreased over time to lessen the charge delivered to the electrode 50. Further, it is possible to "ramp-up" and "ramp-down" for zero seconds, which indicates that there is no ramping.

This "ramping-up" and "ramping-down" is illustrated even further with reference to the stimulation pulse train T which is provided in correspondence with the envelope B2 of the channel E2. In accordance with the envelope B2, the pulse P of the pulse train T first may gradually increase in pulse duration PD, then may maintain the maximum pulse duration PD for a select duration, and finally may gradually decrease in pulse duration PD.

As mentioned, the current I, pulse duration PD, pulse frequency PF, and envelope B1-B2 may be adjustable for every stimulation channel E, independently of the other channel. The waveform shape (e.g., rectangular, exponential, ramp; pre-pulse, post-pulse) and channel synchrony (i.e., when stimulation through each channel starts and stops with respect to the other channels) may also be adjustable. The stimulation pulse generator circuit 60 may be pre-programmed with one or more stimulation patterns, which may allow a patient to select the prescribed one of the patterns as required or otherwise desired during therapy. The pulse train, however, does not have to be constant (e.g., frequency may vary). Additionally, the ramping parameters may be adjusted (e.g., off time, ramp up time, ramp down time, and hold time).

In some embodiments, the pulse generator 10 may include at least two stimulation pulse channels E. The stimulation pulse trains T of each channel E may be sequentially or substantially simultaneously transmitted to their respective electrodes 50. The pulse frequency PF may be adjustable within the range of approximately 1 Hz to approximately 100 Hz; the cathodic amplitude PA may be preferably adjustable within the range of approximately 0.1 mA to approximately 40 mA; and, the pulse duration PD may be preferably adjustable in the range of approximately 1 μsec to approximately 500 μsec delivered by the circuit 60.

In alternative embodiments, the pulse generator may be implantable into a patient's body and would generate stimulation in a similar fashion as described previously for an external stimulator. In such embodiments, the pulse generator may be implanted in any appropriate location of a patient's body, including, without limitation, within the back, legs, torso and the like. With an implantable pulse generator, both the generator and the electrodes (and leads, if applicable) are underneath the skin. As a result, a programmer may communicate with the stimulator through the skin. Prior to placing the implantable pulse generator, a patient may use a percutaneous system as a trial.

Figure 4:
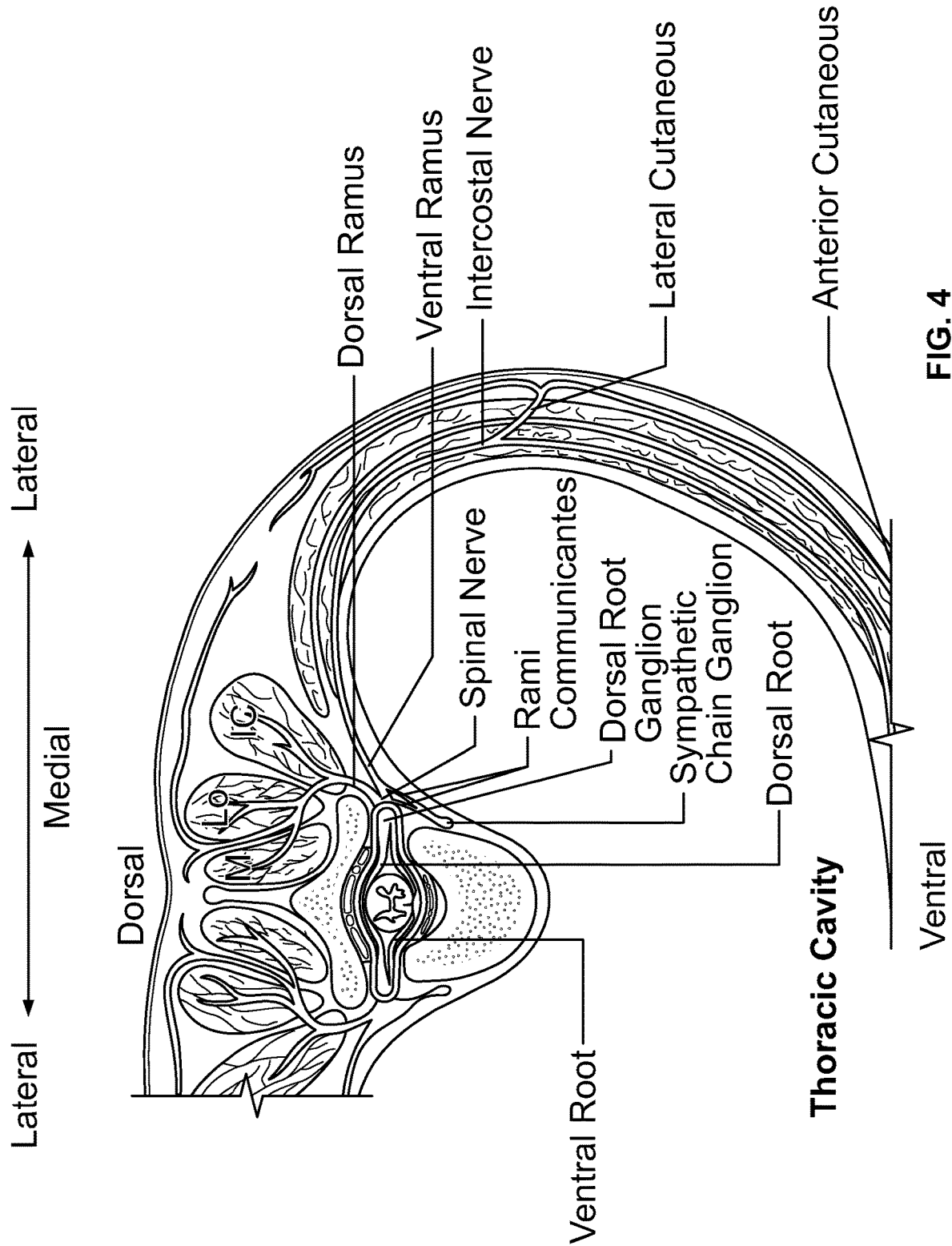
FIG. 4 is a cross-sectional view of the innervation of paraspinal muscles.
Figure 5:
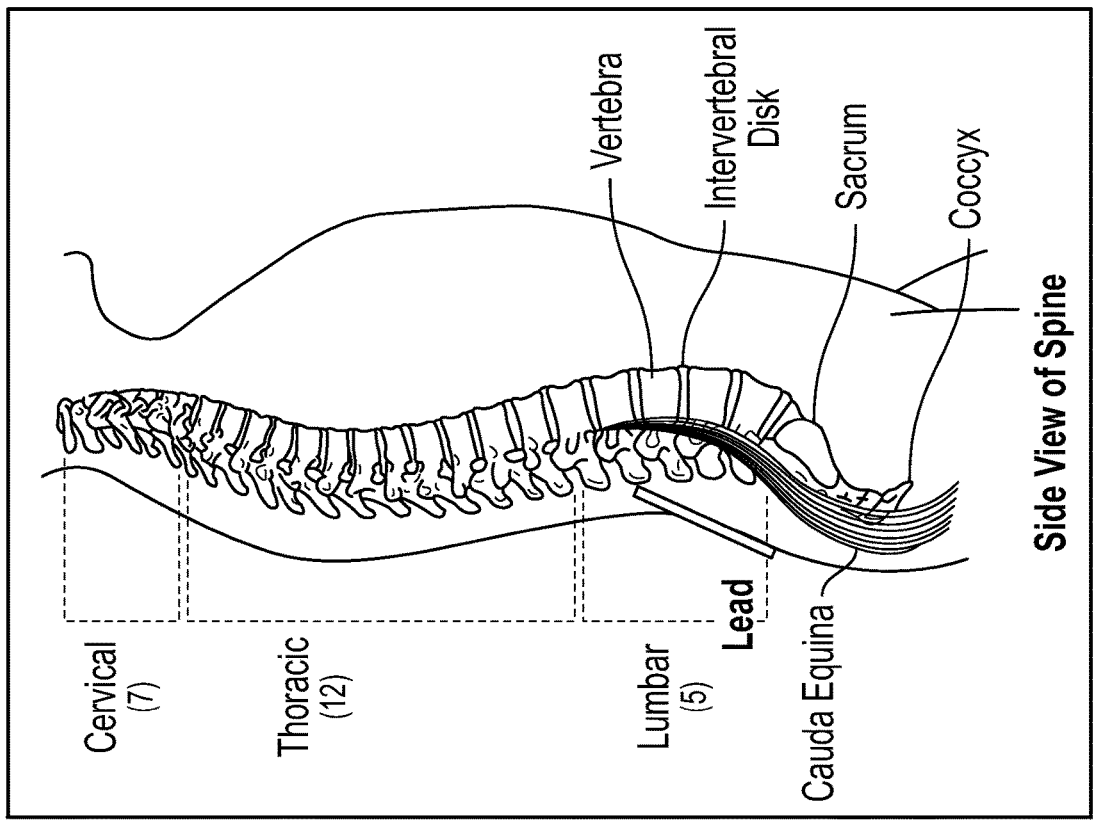
FIG. 5 is two different side views of the insertion of a lead into an animal body.
Figure 5:
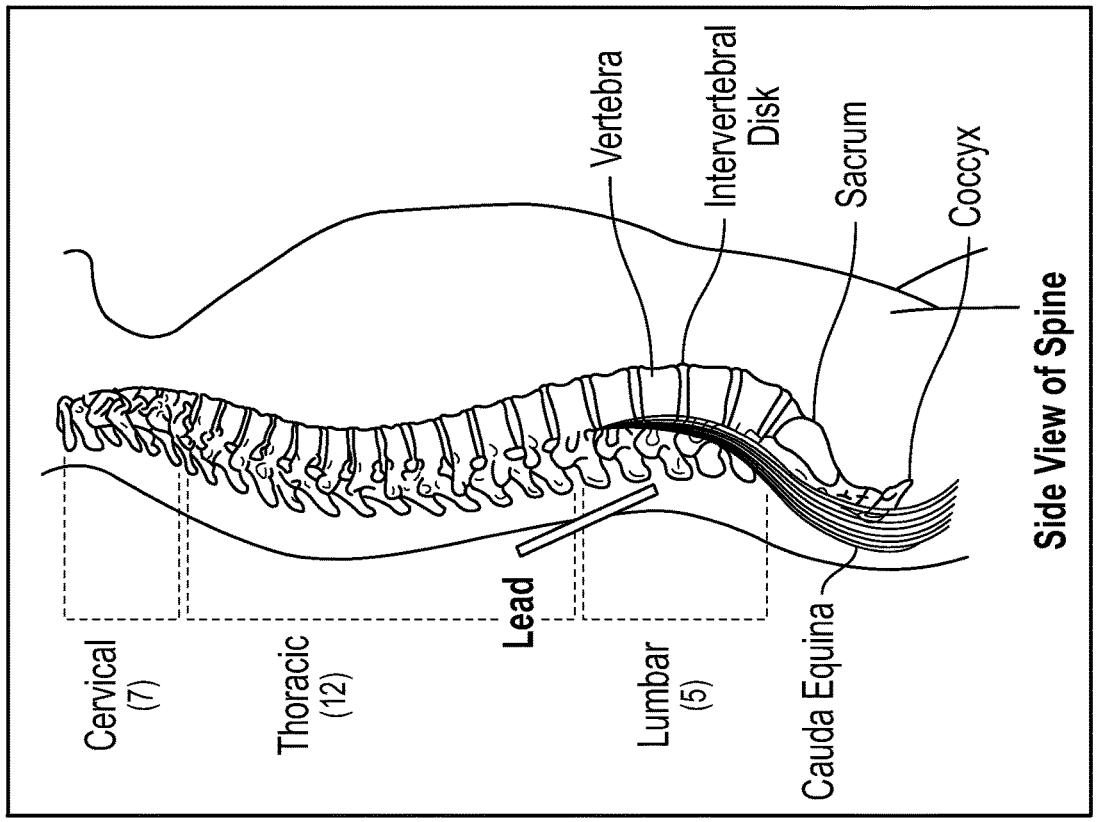

According to one method of treatment according to the present teachings, percutaneous leads may be placed in the erector spinae muscles (see FIG. 4), although this approach may be generalized to any muscle in the back, including, but not limited to, longissimus, iliocostalis, spinalis, multifidus, latissimus dorsi, rhomboid, serratus posterior, oblique external, oblique internal, quadratus lumborum, psoas major, psoas minor, trapezius, levator scapulae, splenius capitis, splenius cervicis, semispinalis muscles, rotatores muscles, rectus capitis posterior muscles, interspinales, levatores costarum, obliquus capitis inferior muscle, obliquus capitis superior, rectus capitus posterior major, and rectus capitus posterior minor, and the leads may be placed in any tissue. First, the most painful regions on each side of a patient's back may be determined through patient-drawn diagrams of pain, verbal description of location of pain, manual evaluation, and/or other methods. Specifically, a clinician may use his/her fingers to gently palpate the back, starting within the regions indicated on a pain diagram previously completed by the patient, and the patient may indicate where pain is greatest on both the left and/or right sides. Once the most painful regions are located, the skin on these regions may be prepared with antiseptic. On one or both sides of the back at the most painful regions, a sterile needle electrode (i.e., test needle) may be inserted into the erector spinae muscles and connected to an external pulse generator to deliver electrical stimulation (see FIGS. 5, 7A-7J). Alternatively, the electrode may not be connected to a pulse generator (e.g., the generator may be integrated or pre-connected with the electrode (Bion®) or it may be radio frequency or otherwise wirelessly powered). The electrode may be placed at the same spinal level (e.g., L3, S1) as the most painful areas but a fixed distance (e.g., 2.5 cm) from the body's midline. Yet another approach may be to insert the needle at an angle at a different site (on the dorsal/posterior, lateral, or ventral/anterior part of the body), so that the tip of the needle may be positioned within the muscles directly beneath the site of the greatest pain (see FIG. 5). Needle insertion may be guided by ultrasound, fluoroscopy, or any other appropriate method. The depth of the needle insertion may be guided by MRI scans or electromyography or by other known procedures for insertion of needles or the like into the back (e.g., paravertebral injections).

Intensity of the electrical stimulation provided by the pulse generator may be increased on each side or on a single side to reach comfortable muscle contraction (e.g., evaluated visually by movement of muscle, needle motion or utilizing an imaging modality such as ultrasound, thermal, infrared, MRI/PET, or biophotonics, by manual palpation, by non-human palpation, by electromyography, by computer-aided visualization, by changes in electrical conductivity of tissue or by patient report of muscle contractions). Alternatively, muscle contractions may be generated but may not be able to be observed by the same means. For example, patients may describe experiencing sensations that are associated with muscle contractions, including, but not limited to, tapping, tightening, pinching, pricking, or massaging. Once contractions have been evoked, the location of the needle insertion may be marked, the needle removed, and the positioning of the needle (e.g., depth beneath skin, angle with respect to surface of the skin) may be measured. In other embodiments, stimulation may proceed without confirmation of muscle contractions. For example, a clinician may use a strong intensity likely to cause muscle contractions, but the clinician may choose not to verify that muscles have contracted.

Figure 6:
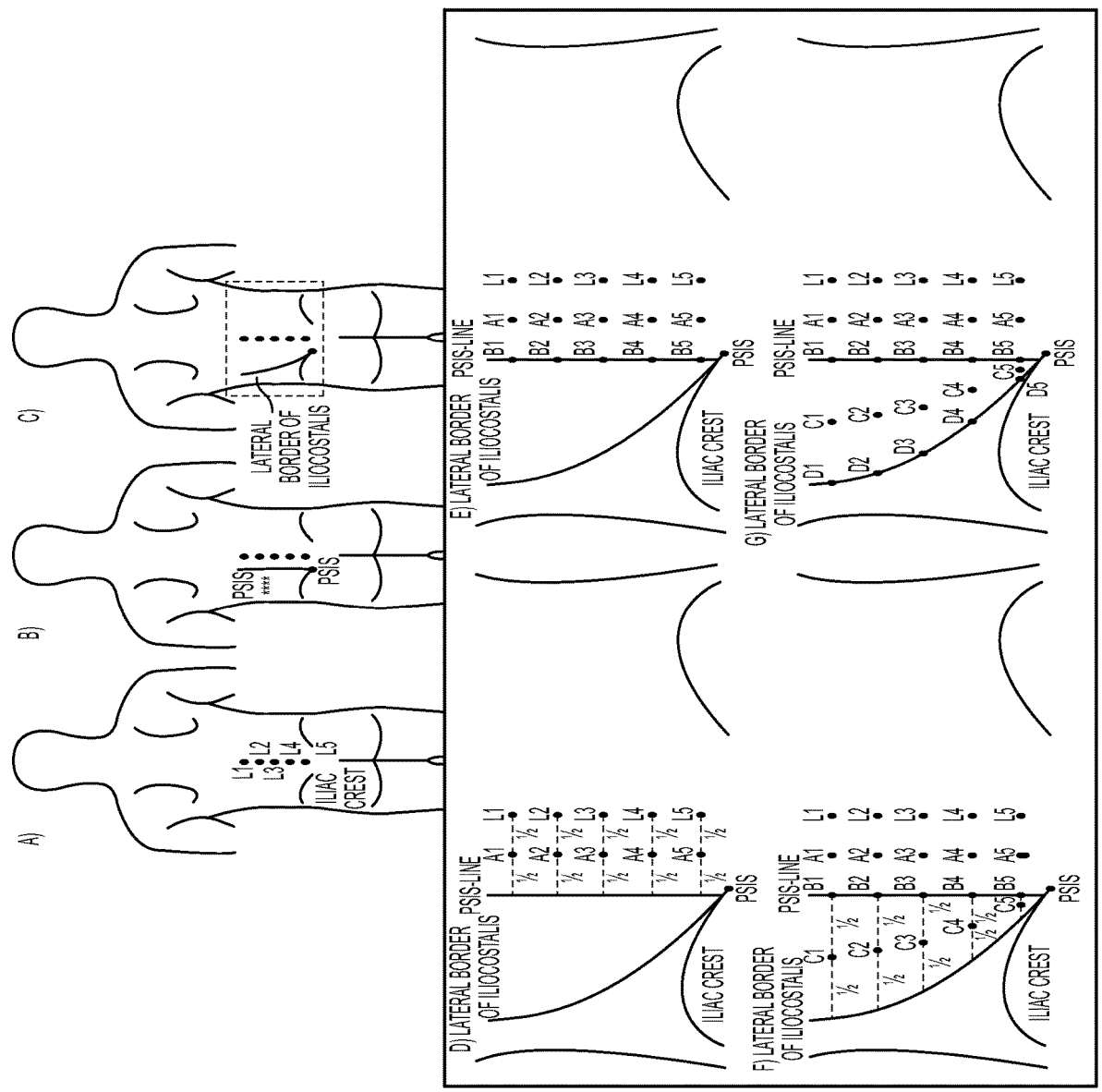
FIG. 6 is an example of a coordinate system to guide electrode placement based on anatomical landmarks including the posterior superior iliac spine (PSIS)

As shown in FIG. 6, percutaneous leads may be placed through entry points on a patient. An introducer may be used at the site or sites identified with the needle electrodes and may be placed at the depth identified previously and using the needle positioning identified previously or the method may be completed without a test needle. Electrode placement may be guided by a predetermined map of muscle response generated by stimulation at different coordinates, where the coordinates may be based on relative or absolute distances from anatomical landmarks. This predetermined map may be individualized for each patient or may be generalized for use across specific groups of patients (e.g., obese patients, tall patients, geriatric patients) or all patients. The patient may be given lidocaine along the anticipated pathway of the percutaneous lead if he or she desires. The leads may be inserted and connected to an external pulse generator of any appropriate configuration. Stimulation may be delivered through the leads to verify proper placement (e.g., stimulation-evoked muscle contractions). The introducers may be removed, leaving the leads within the target tissues. Following placement, the proximal portion of the lead, which may reside outside of the patient's body, may be secured to the skin and covered with a waterproof bandage. Prior to leaving the clinic, a patient may be instructed on the proper care of the lead exit sites. Patients may be inspected afterwards (e.g., within 48 hours) for analysis of the leads and exit sites. The leads may be allowed to stabilize for one week before the treatment period begins.

Figure 7A:
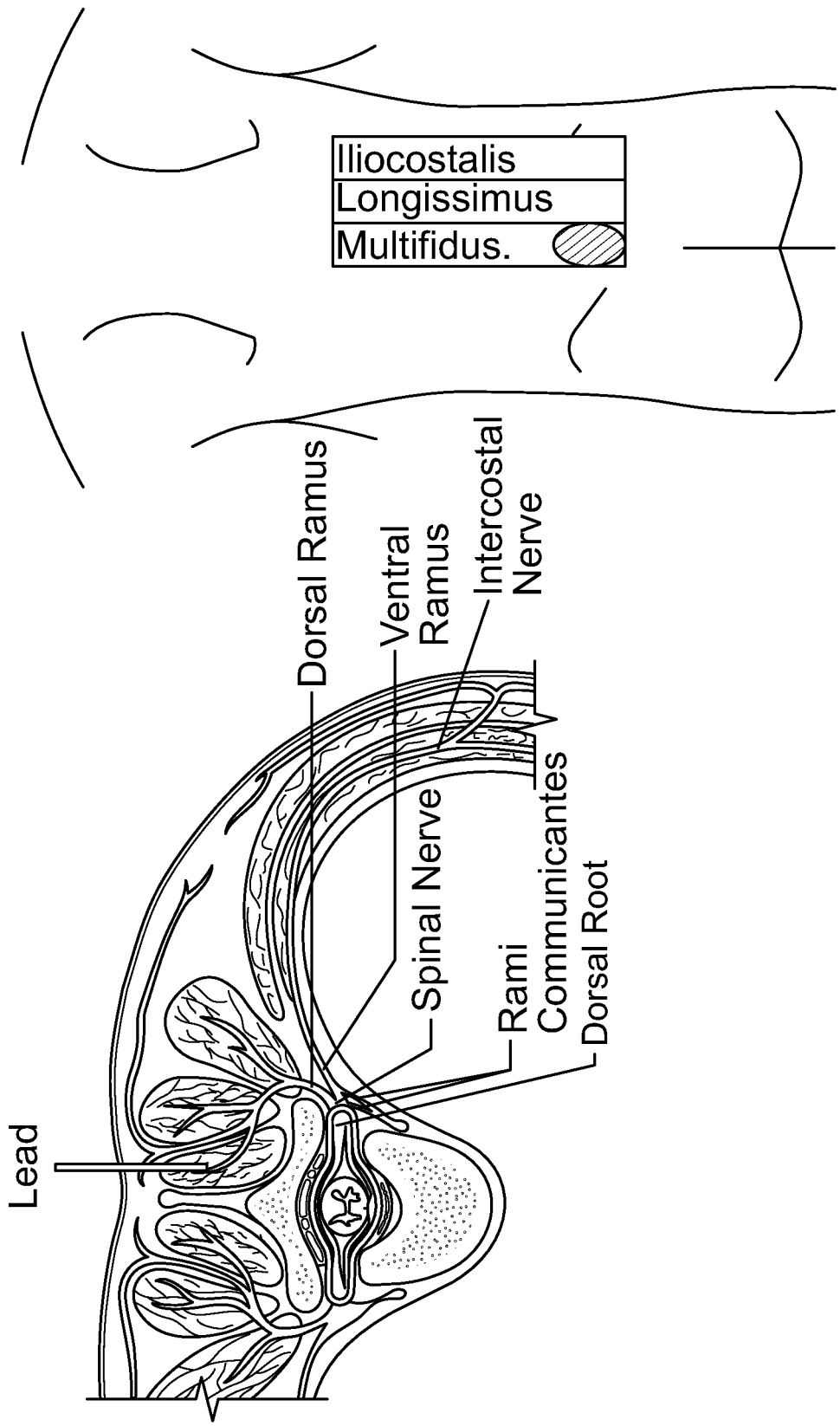
FIGS. 7A-7J illustrate placement of the percutaneous lead(s) into the muscles of the back and the associated regions of muscle activation.
Figure 7B:
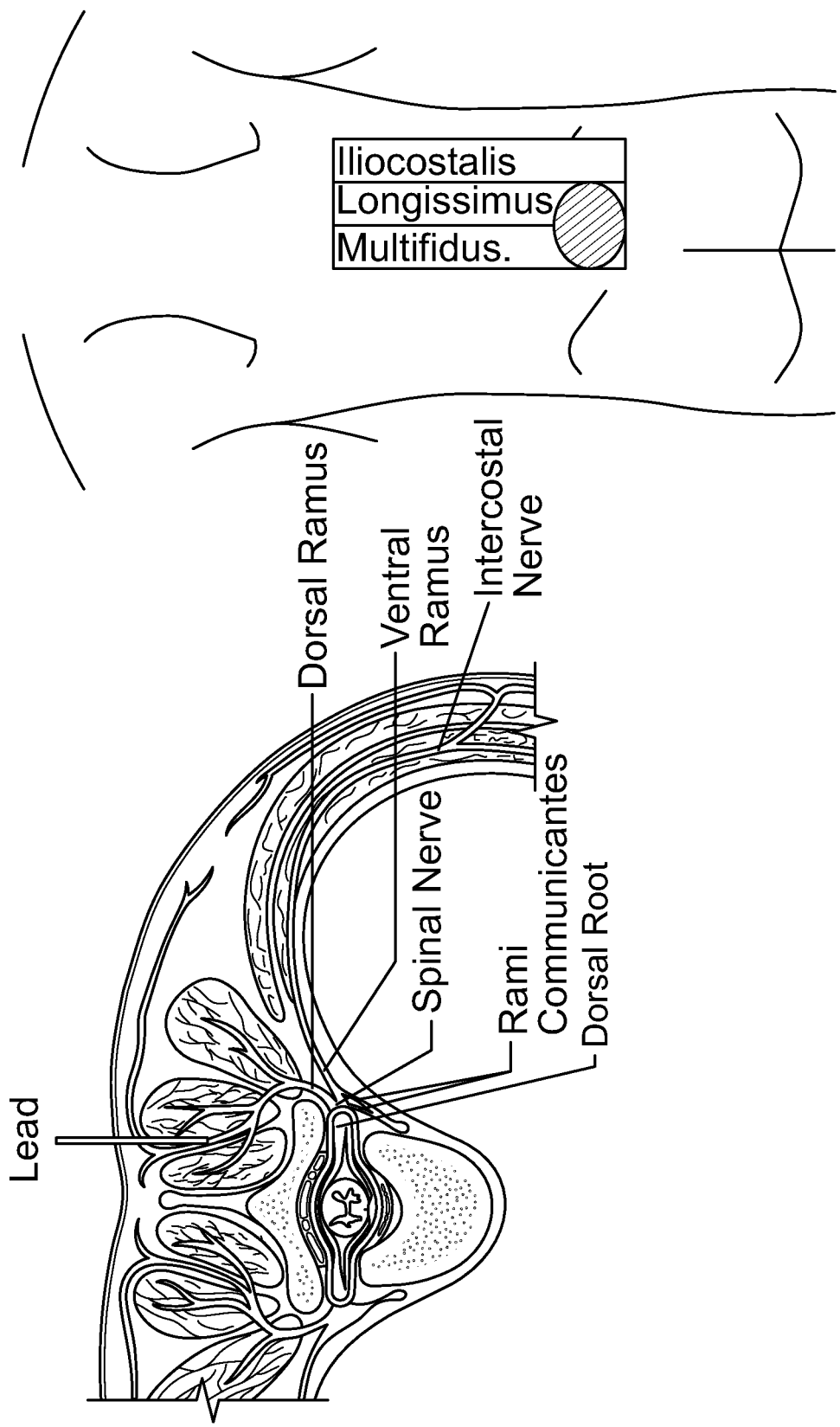
Figure 7C:
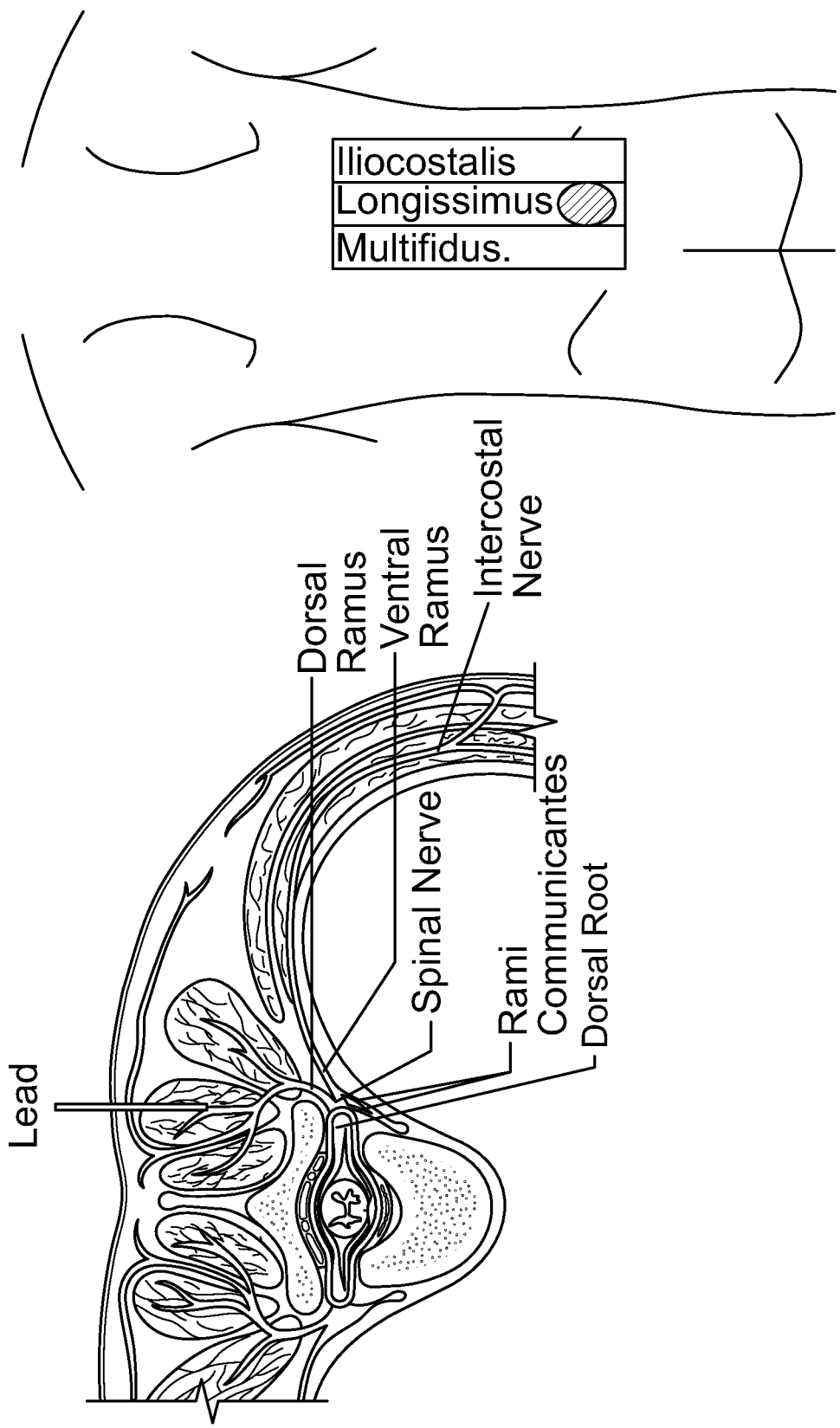
Figure 7D:
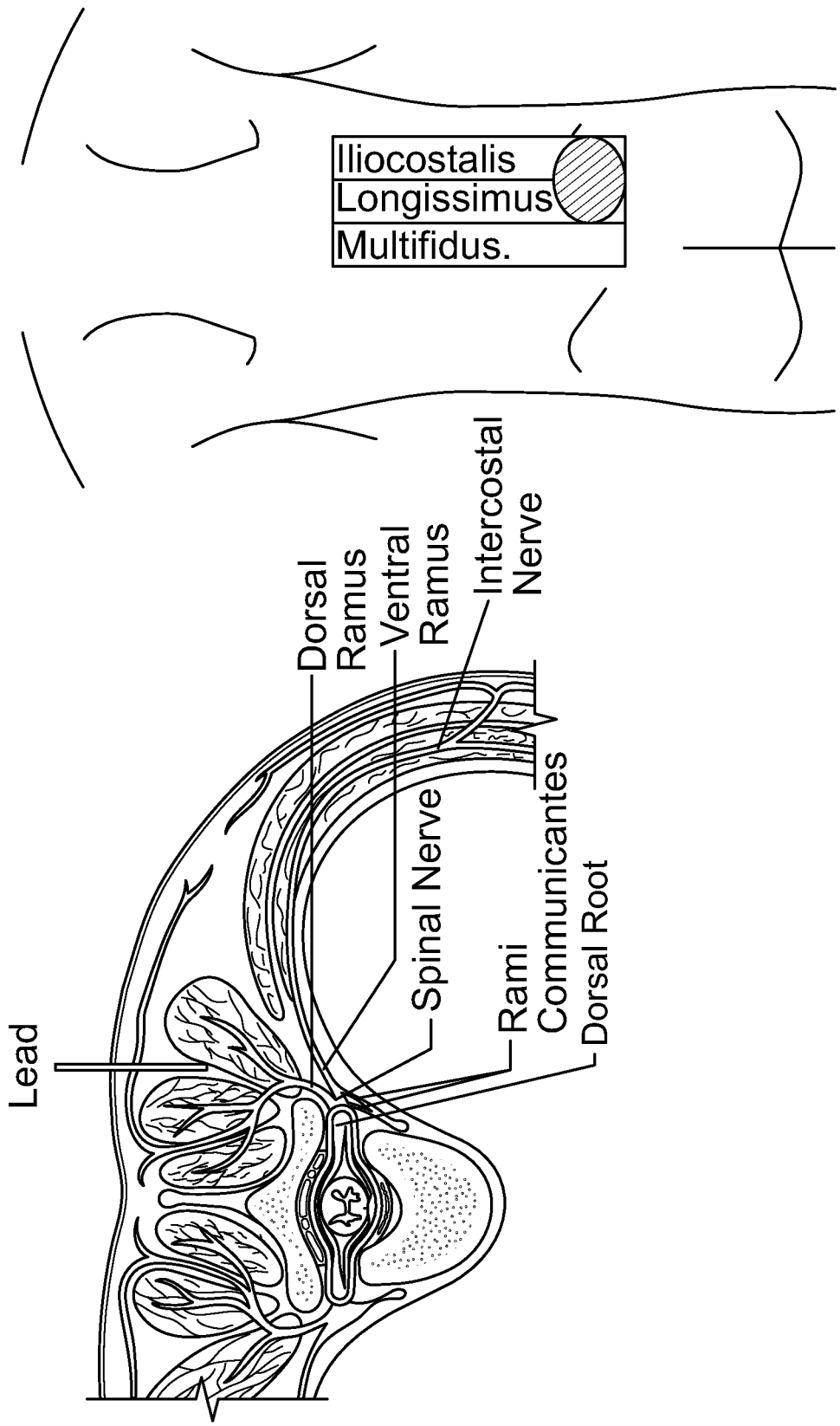
Figure 7E:
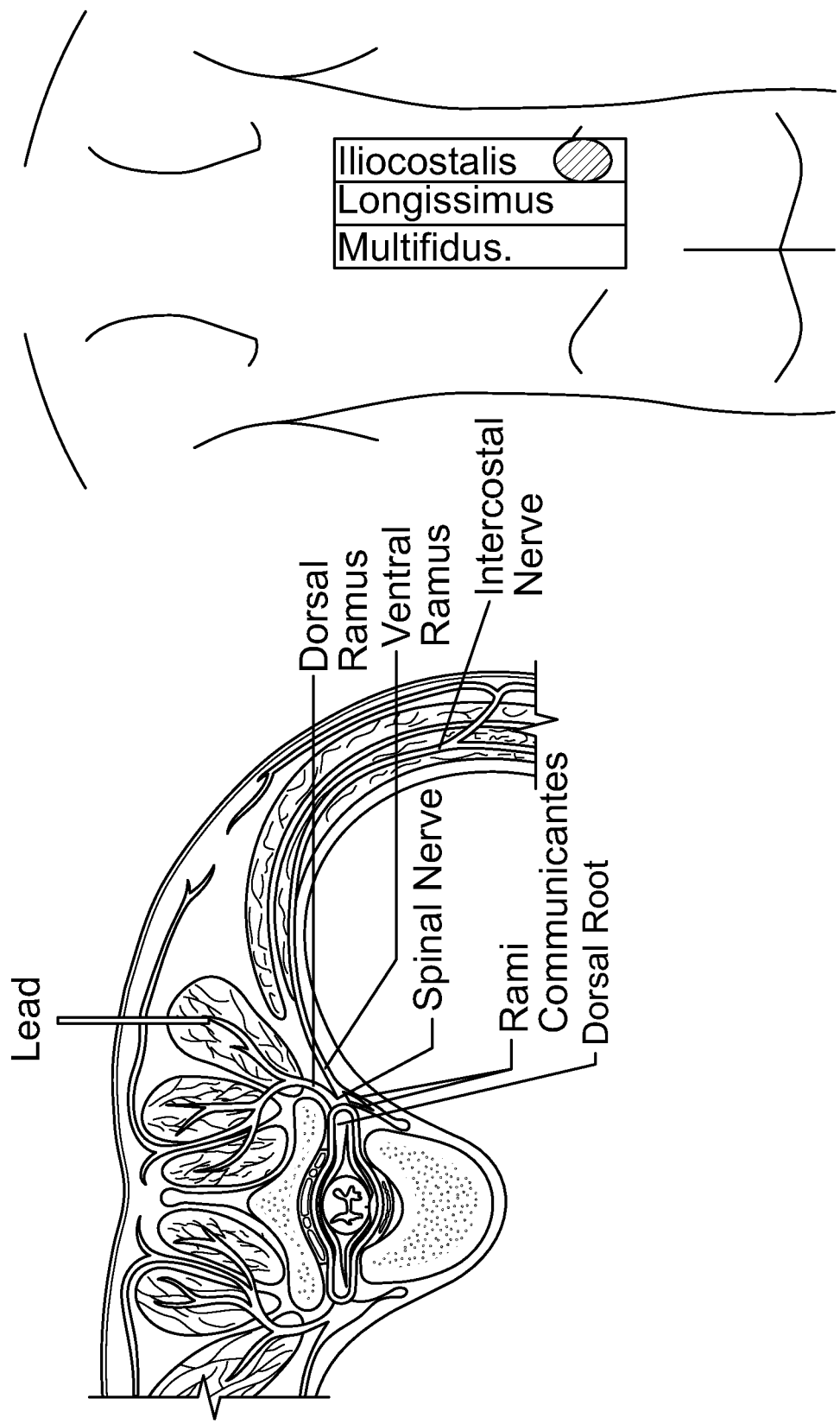
Figure 7F:
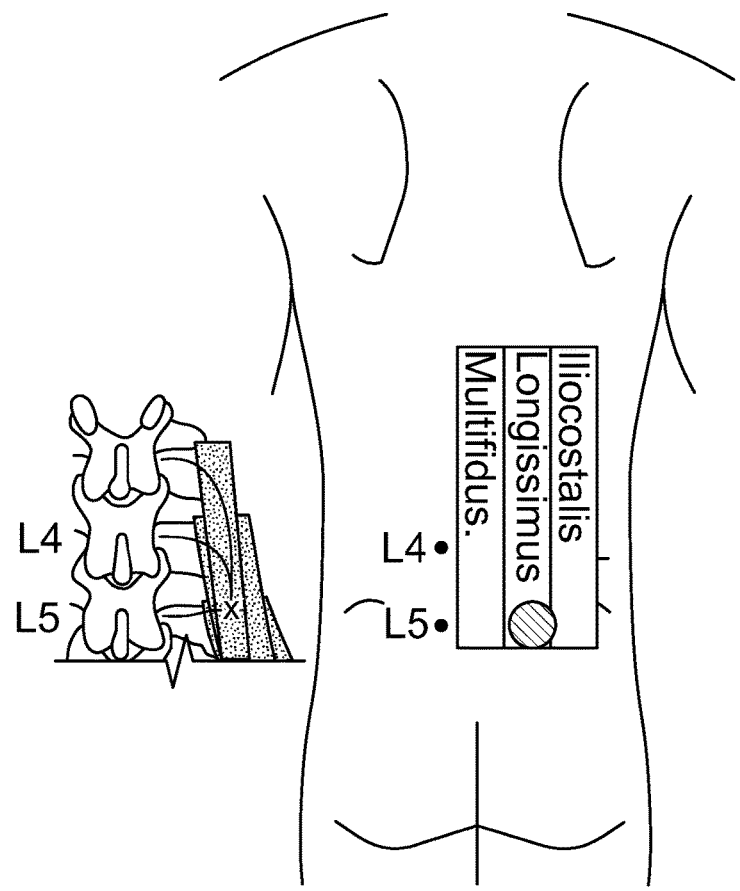
Figure 7G:
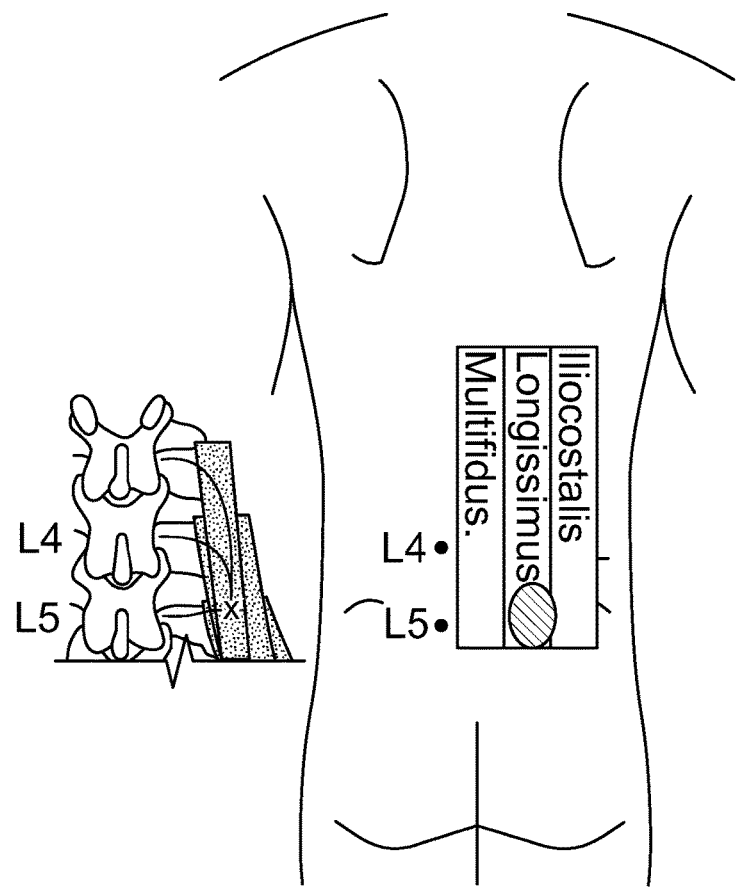
Figure 7H:
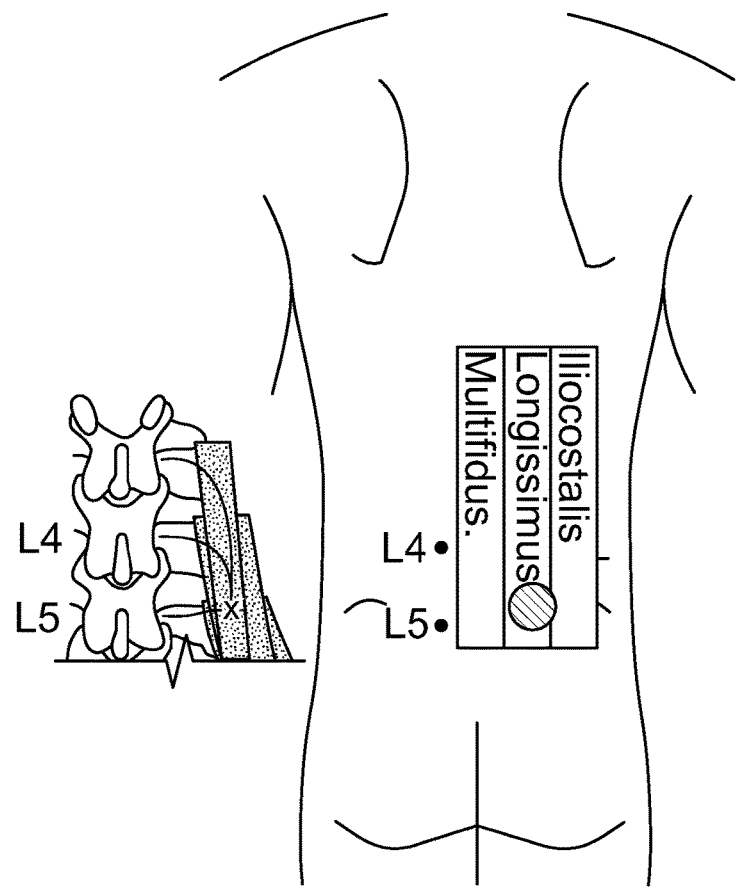
Figure 7I:
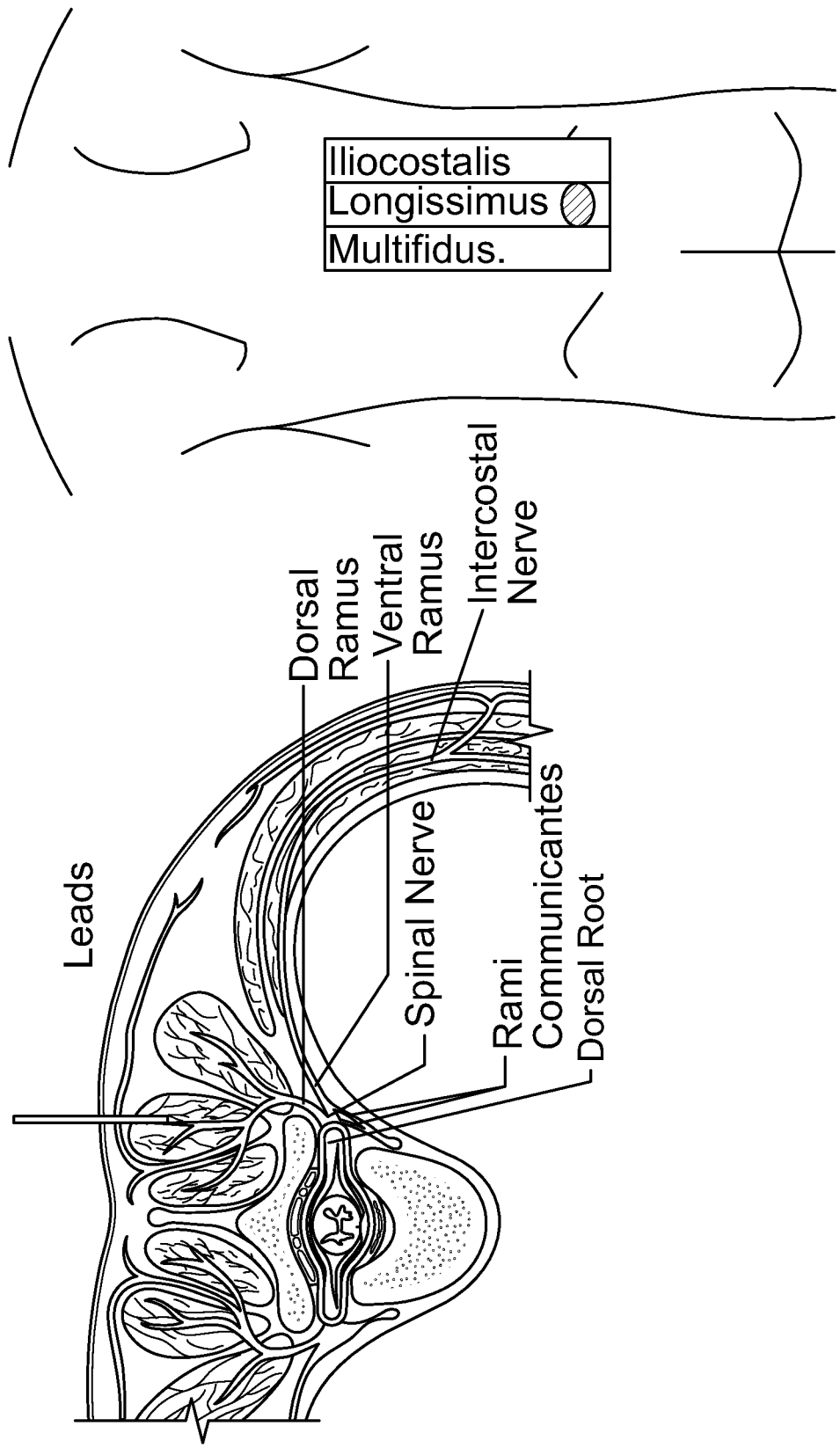
Figure 7J:
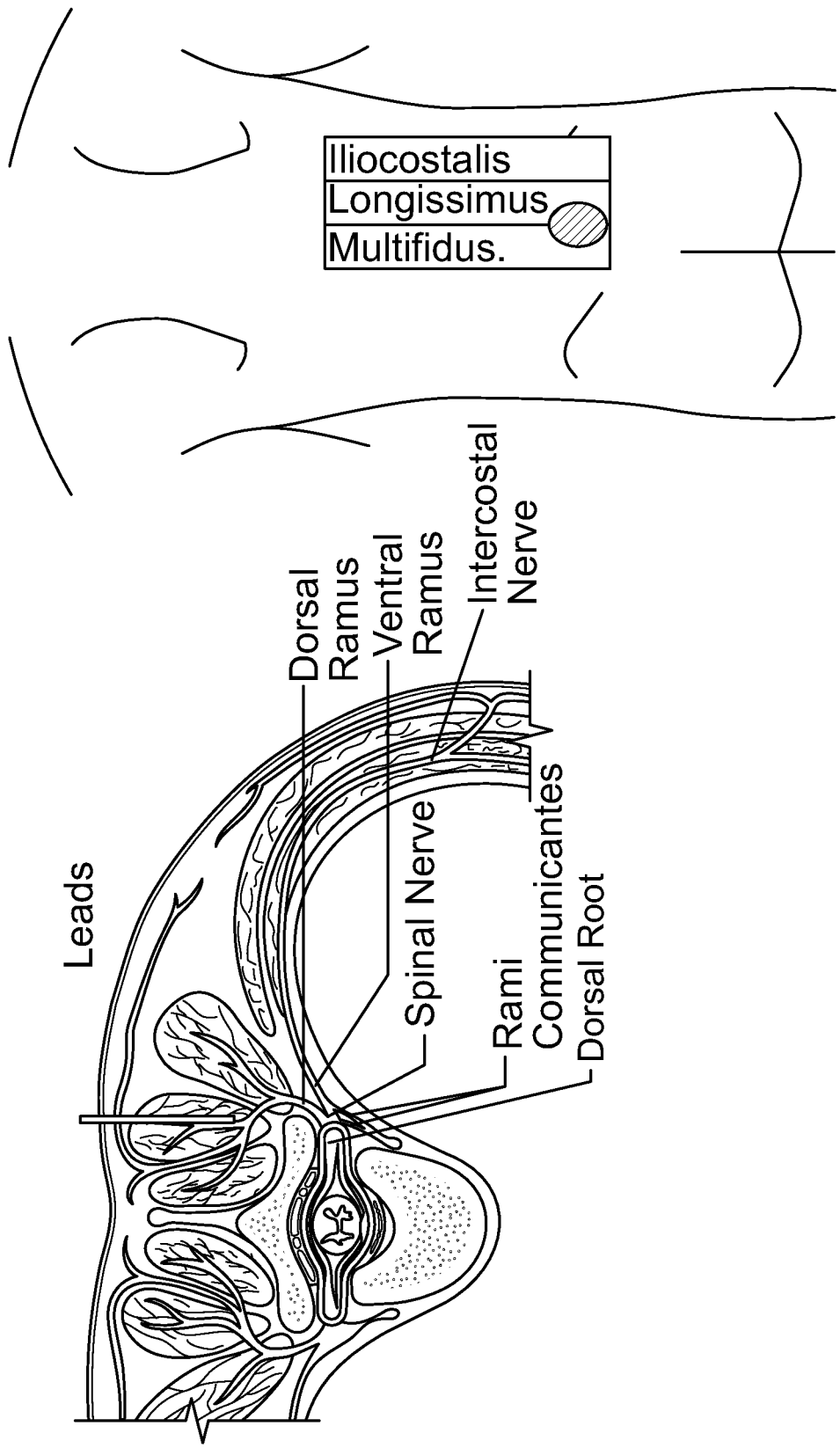

The lead may need to be repositioned to generate comfortable muscle contractions in a different part of the back, and this may be achieved based on known innervation patterns for the paraspinal muscles or any other appropriate muscle or muscle group. For example, because the medial, intermediate, and lateral branches of the dorsal ramus innervate lumbar paraspinal muscles positioned in the same medial-lateral order (i.e., multifidus, longissimus, iliocostalis) (FIG. 4), the lead may be repositioned medially or laterally to generate more medial or lateral muscle activation, respectively (FIGS. 7A-E). Similarly, because the paraspinal muscles are segmentally innervated, the lead may be repositioned more superior or inferior to generate more superior or inferior muscle activation, respectively (FIGS. 7F-H). The depth of the lead may also generate different regions of muscle activation due to the branching patterns of the dorsal ramus (FIGS. 7C, 7I, and 7J).

The approach according to the present invention, using one or more percutaneous leads placed in tissue to cause muscle contraction, may avoid cutaneous discomfort since stimulation is delivered away from cutaneous receptors and closer to target peripheral motor neurons. While activation of motor axons causes muscle activation, it may not be expected to cause discomfort. The branches of the dorsal rami innervating the paraspinal muscles contain not only motor axons, but also sensory axons. Motor axons typically have a larger diameter than the sensory axons that transmit the signals that lead to the perception of pain. The strength (i.e., intensity) of electrical stimulation required to activate axons increases as axon diameter decreases. Thus, motor axons should be activated at lower stimulation intensities than sensory axons, enabling comfortable activation of motor axons without activation of painful sensory axons. Further, because of the placement of the leads subcutaneously within tissue, electrical stimulation may be delivered far from cutaneous receptors and may avoid the painful sensations generated during other methods, such as TENS.

Figure 8:
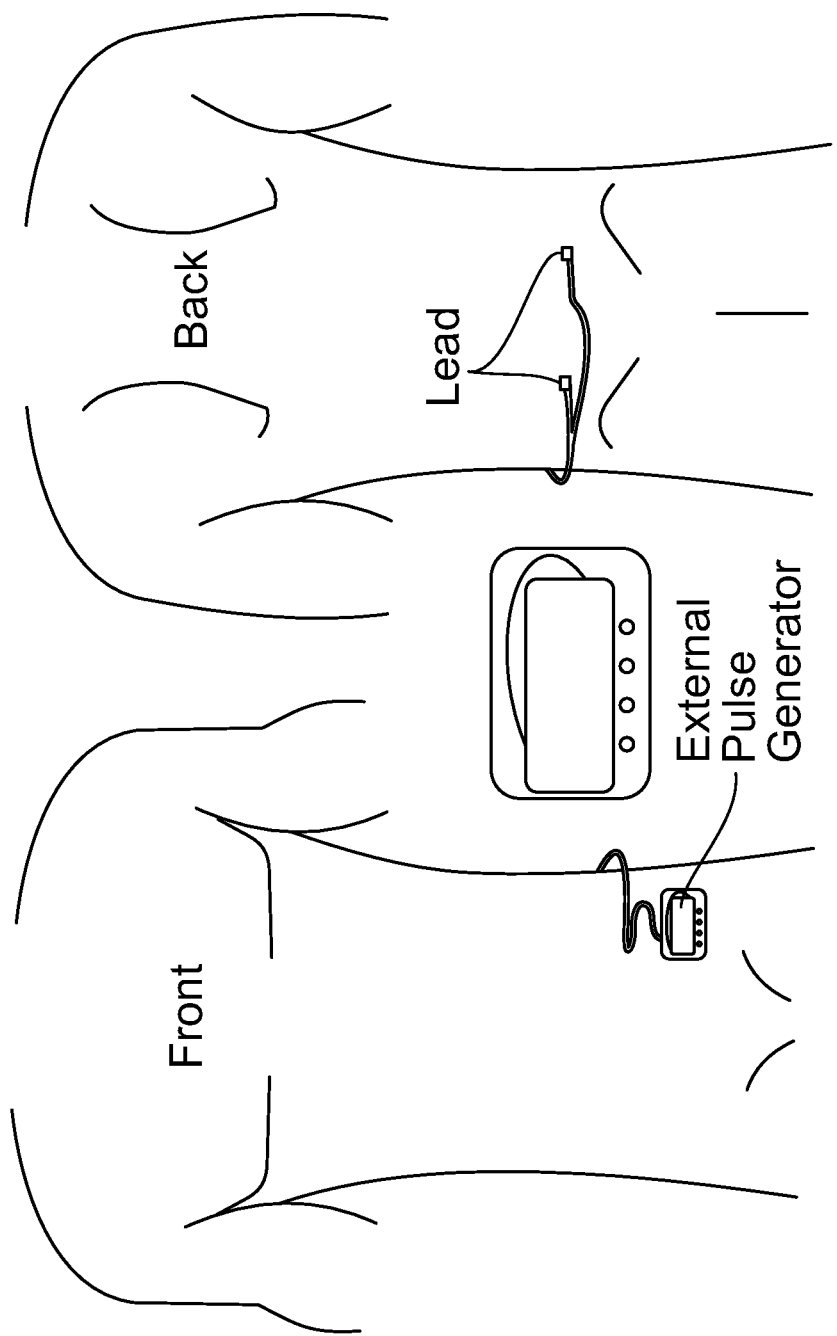
FIG. 8 illustrates placement of the percutaneous leads and pulse generators on a patient's body.

Stimulation frequency and amplitude of the stimulation applied may be variable, but in some embodiments may be fixed. Intensity may be modulated by varying the pulse duration. Stimulation intensity may be set to generate strong, comfortable muscle contractions. As shown in FIG. 8, each of the two percutaneous leads may be wrapped around a patient's respective side and connected to a pulse generator, such as a body-worn external pulse generators located on the front or side of the abdomen. In other embodiments, the external pulse generator may be placed on any appropriate location, including, without limitation on the back, legs, or arms. Over the treatment period, such as three weeks, a patient may self-administer stimulation every day for a daily treatment time, such as a total of six hours/day (e.g., either two 3-hour sessions, or one 6-hour session). Patients may be able to partake in their normal routines during stimulation. A patient may use the system in any bodily position (e.g., while sitting, standing or laying down (supine, prone, or laying down on one's side)). The stimulator may maintain an electronic log for compliance monitoring. In other embodiments, stimulation may be administered under the guidance of a clinician (e.g., in an office, or clinic). At the end of the treatment period, the leads may be removed in any appropriate manner, such as by applying gentle fraction.

Use of systems and methods according to the present teachings may be expected to generate comfortable targeted activation of back muscles anywhere there is pain, including, without limitation the lumbar, thoracic, cervical and sacral levels. Percutaneous electrical stimulation may be expected to generate comfortable targeted activation of muscles that overlap the region of greatest pain. The activation of back muscles may also be generated near, but outside of the region of pain. The location of the target back muscles may be unrelated to the region of pain and may be selected based on other criteria (e.g., patient age, weight, height, medical history) or may be the same for all patients. The pain may be acute, subacute, or chronic back pain. If the stimulation is used to treat acute or subacute pain, it may be used to prevent chronic pain in the future.

Contraction of muscles may be evoked using electrical stimulation in many ways. Electrical stimulation may be used to activate motor axons that innervate the muscle and cause activation and contraction of the muscle. Stimulation may also be used to stimulate motor points of muscles, where motor axons enter a muscle. Stimulation may also be used to activate the muscle directly without activation of the motor axons. However, threshold stimulation intensities for activation of motor axons may typically be lower than that of direct activation of muscle. Electrical stimulation may also be used to stimulate other parts of the body to cause a reflex response that activates the target muscle. Stimulation may also be used to activate muscle by stimulation of the dorsal root of spinal nerve, ventral root of spinal nerve, dorsal root ganglion, spinal nerve, and/or the spinal cord. Stimulation may also be used to activate a structure that is not in the back (e.g., abdominal muscle, shoulder muscle) that causes passive movement (e.g., stretching, compression, torsion) of a back muscle.

During the treatment period (e.g., three weeks) the treatment may reduce pain while stimulation is on, and may lead to reduced pain while stimulation is off. The muscle contraction is thought to provide pain relief that may also persist after the treatment period (carryover effect) for several minutes to several months. Thus, this temporary (e.g., three weeks) treatment may provide long-term pain relief at least as long as the treatment period itself (e.g., three weeks to one year). Further, this treatment may cause change to the nervous system that relieves pain.

Compared to individuals with healthy backs, patients with chronic back pain have reduced function, health-related quality of life, and range of motion. When treatments reduce chronic back pain, function, health-related quality of life, and range of motion improve. As a result, the reductions in chronic back pain generated by the invention may be expected to result in improvements in function and significant improvements in health-related quality of life and range of motion. When combined with other back pain therapies, may enhance overall effectiveness.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof.

The invention claimed is:

1. A method to alleviate back pain, the method comprising:
    percutaneously inserting a lead having a single electrode within a tissue of an animal body, the lead having an insulated and a deinsulated portion wherein the electrode is formed from the deinsulated portion; and
    applying an intensity of electrical stimulation through the single electrode to activate motor axons of at least one muscle in a back of the animal body with back pain causing muscle contraction of the at least one muscle without activation of painful sensory axons relieving the back pain of the animal body.

2. The method of claim 1, further comprising evaluating the electrical stimulation by identifying an area of pain.

3. The method of claim 1, further comprising the step of inserting the at least one electrode at a location based on an area of the back pain.

4. The method of claim 3, wherein the electrode is placed at a spinal level at the same level as a site of greatest pain.

5. The method of claim 2, further comprising comparing an area of muscle activation caused by the electrical stimulation with the area of pain.

6. The method of claim 5, further comprising:
    repositioning the single electrode;
    applying electrical stimulation through the repositioned single electrode; and
    re-comparing a second area of muscle activation caused by the electrical stimulation with the area of pain.

7. The method of claim 5, further comprising:
    applying a first set of electrical stimulation parameters;
    comparing a second area of muscle activation caused by the electrical stimulation with the area of pain; and
    applying a second set of electrical stimulation parameters.

8. The method of claim 7, wherein the first and second set of electrical stimulation parameters are selected from a group consisting of:
    frequency, pulse duration, amplitude, duty cycle, pattern of stimulus pulses, polarity, number of phases, and waveform shape.

9. The method of claim 1, wherein the region of back pain in the animal body is selected from a group consisting of: sacral, lumbar, thoracic and cervical levels.

10. The method of claim 1, wherein the alleviation of back pain persists after the stimulation is discontinued.

11. The method of claim 1, further comprising:
    inserting one additional electrode;
    applying electrical stimulation through the one additional electrode; and
    comparing an area of muscle activation caused by the electrical stimulation with an area of pain.

12. The method of claim 11, further comprising:
    removing the single electrode;
    applying an electrical stimulation through the one additional electrode; and
    re-comparing a second area of muscle activation caused by the electrical stimulation with the area of pain.

13. The method of claim 1, further comprising:
    turning on a channel of the single electrode;
    applying electrical stimulation through the single electrode; and
    comparing an area of muscle activation caused by the electrical stimulation with an area of pain.

14. The method of claim 13, further comprising:
    turning off a channel of the single electrode;
    applying an electrical stimulation through the single electrode; and
    re-comparing a second area of muscle activation caused by the electrical stimulation with the area of pain.

15. The method of claim 1, wherein the electrical stimulation affects change in a nervous system of the animal body.

16. The method of claim 15, further wherein the change in a nervous system of an animal body relieves pain.

17. The method of claim 1, further comprising the step of positioning the at least one electrode at a location in proximity to and outside of a region of pain of the animal body.

18. The method of claim 1, further comprising the step of positioning the at least one electrode at a location unrelated to a region of pain of the animal body.

19. The method of claim 18, wherein the location is selected based on criteria other than pain.

\* \* \* \* \*